United States Patent
Kasuya

(10) Patent No.: US 7,760,850 B2
(45) Date of Patent: Jul. 20, 2010

(54) X-RAY COMPUTED TOMOGRAPHIC APPARATUS

(75) Inventor: Yuichi Kasuya, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 122 days.

(21) Appl. No.: 12/236,998

(22) Filed: Sep. 24, 2008

(65) Prior Publication Data
US 2009/0080599 A1     Mar. 26, 2009

(30) Foreign Application Priority Data
Sep. 26, 2007   (JP) .............................. 2007-250299

(51) Int. Cl.
  *H05G 1/60*   (2006.01)
  *A61B 6/03*   (2006.01)
  *G01D 18/00*  (2006.01)
(52) U.S. Cl. ......................................... 378/15; 378/207
(58) Field of Classification Search .................. 378/15, 378/207
See application file for complete search history.

(56) References Cited

U.S. PATENT DOCUMENTS

| | | | |
|---|---|---|---|
| 4,276,490 A * | 6/1981 | Saldinger | 310/184 |
| 6,169,778 B1 * | 1/2001 | Schmidt et al. | 378/15 |
| 6,553,091 B2 * | 4/2003 | Takanashi et al. | 378/15 |
| 6,590,953 B2 * | 7/2003 | Suzuki et al. | 378/15 |
| 6,590,960 B2 * | 7/2003 | Kroener et al. | 378/162 |
| 7,202,580 B2 * | 4/2007 | Yokoyama et al. | 310/68 B |

* cited by examiner

*Primary Examiner*—Allen C. Ho
(74) *Attorney, Agent, or Firm*—Oblon, Spivak, McClelland, Maier & Neustadt, L.L.P.

(57) ABSTRACT

An X-ray computed tomographic apparatus includes a rotary frame, a mechanism which rotatably supports the rotary frame, an X-ray tube which is mounted to the rotary frame, an X-ray detector which is mounted to the rotary frame, a plurality of rotor magnets which is arranged in the rotary frame, a plurality of stator coils which is opposed to the rotor magnets, an MR sensor which detects a magnetic-flux variation accompanied by a movement of the rotor magnets, and a position specifying unit which specifies a magnetic-pole position of each rotor magnet with respect to each stator coil on the basis of an output of the MR sensor and a convergence time from a vibration start of the rotary frame caused by a short-time excitation of the stator coil to a vibration stop of the rotary frame.

13 Claims, 4 Drawing Sheets

EXCITATION STOP
(VIBRATION START)

VIBRATION
(CONVERGENCE)

VIBRATION END
(STOP)

X-RAY COMPUTED TOMOGRAPHIC APPARATUS

CROSS-REFERENCE TO RELATED APPLICATIONS

This application is based upon and claims the benefit of priority from prior Japanese Patent Application No. 2007-250299, filed Sep. 26, 2007, the entire contents of which are incorporated herein by reference.

BACKGROUND OF THE INVENTION

1. Field of the Invention

The present invention relates to an X-ray computed tomographic apparatus in which a direct-drive (DD) motor is mounted to a gantry.

2. Description of the Related Art

In the past, X-ray computed tomographic apparatuses have been widely used in order to obtain a tomographic image of a subject. In most of current X-ray computed tomographic apparatuses, an X-ray tube and an X-ray detector are configured to continuously rotate around the subject. A gantry is provided with a motor rotationally driving an annular rotary frame mounted with the X-ray tube and the X-ray detector. In recent years, an X-ray computed tomographic apparatus has been distributed in which a direct-drive (DD) motor is used as the motor.

The direct-drive motor mainly includes a plurality of stator coils arranged in a fixed part in a circumferential shape and a plurality of rotor magnets arranged in the inside thereof so as to be opposed to the stator coils. A pulse signal is supplied from a servo amplifier to the stator coil at a frequency in accordance with a coil arrangement and a necessary speed. Accordingly, it is necessary to accurately adjust the polarity change timing of the pulse signal in accordance with a position of the rotor magnet with respect to the stator coil, that is, a distance between a center position of the stator coil and a center position of the rotor magnet and its direction in a stop state (hereinafter, referred to as a magnetic-pole position).

In the past, a hall IC or a photo sensor is used to detect the magnetic-pole position.

However, in a method using the hall IC, it is necessary to provide a hall IC disposed between a stator motor coil and a rotor magnet, a substrate mounted with the hall IC to extract a signal, a connector, and a cable. Additionally, since it is necessary to ensure some gap between the stator motor coil and the rotor magnet in order to mount the substrate to a position between the stator motor coil and the rotor magnet, the efficiency of the motor deteriorates. Additionally, it is necessary to consider a breakdown of respective electric components.

In a method using the photo sensor, since the number of electric components increases like the method using the hall IC, it is necessary to consider the breakdown. Additionally, since it is necessary to mount a cut plate for a photo sensor and to match an edge position of the cut plate with that of the magnet, the shape is limited. Since it is necessary to ensure a space in a body-axis direction in order to mount the photo sensor, the cut plate, there is a limitation in performing a mounting operation to the apparatus.

BRIEF SUMMARY OF THE INVENTION

An object of the invention is to provide an X-ray computed tomographic apparatus in which a direct-drive motor is mounted to a gantry and which is capable of realizing a simple structure for detecting a magnetic-pole position to save a space, of disposing a stator coil to be adjacent to a rotor magnet, and of easily handling a variation in rotary torque.

According to an aspect of the invention, there is provided an X-ray computed tomographic apparatus including: a rotary frame; a mechanism which rotatably supports the rotary frame; an X-ray tube which is mounted to the rotary frame; an X-ray detector which is mounted to the rotary frame; a plurality of rotor magnets which is arranged in the rotary frame; a plurality of stator coils which is opposed to the rotor magnets; a sensor which detects a magnetic-flux variation accompanied by a movement of the rotor magnets; and a position specifying unit which specifies a magnetic-pole position of each rotor magnet with respect to each stator coil on the basis of an output of the sensor and a convergence time from a vibration start of the rotary frame caused by a short-time excitation of the stator coil to a vibration stop of the rotary frame.

According to the invention, the X-ray computed tomographic apparatus having a direct-drive motor mounted to a gantry is capable of realizing a simple structure for detecting a magnetic-pole position to save a space, of disposing a stator coil to be adjacent to a rotor magnet, and of easily handling a variation in rotary torque.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray computed tomographic apparatus according to an embodiment of the invention will be described in detail with reference to the accompanying drawings. In order to reconstruct one slice of tomographic image data, projection data corresponding to one revolution (about 360°) around a subject is required. Even in a half scanning method, projection data corresponding to 180°+view angle is required. This invention is applicable to any reconstruction type. A mechanism that converts incident X-ray into electric charges mainly includes an indirect conversion method and a direct conversion method. The indirect conversion method converts the X-ray into light using a fluorescent substance such as a scintillator and then converts the light into electric charges using a photoelectric conversion element such as a photodiode. Further, the direct conversion method uses a photoconductive effect, that is, generates an electron-hole pair in a semiconductor by the X-ray and moves into an electrode. Even though any of the methods can be used as the X-ray detecting element, the indirect conversion type will be described in this specification. In recent years, commercialization of products of so-called multi-tube spherical X-ray computed tomographic apparatuses has been progressed in which a plurality of pairs of X-ray tubes and X-ray detectors is mounted on a rotary frame, and the peripheral technologies have progressed accordingly. The present invention is applicable to conventional single-tube spherical X-ray computed tomographic apparatuses and multi-tube spherical X-ray computed tomographic apparatuses. Here, a single-tube spherical X-ray computed tomographic apparatus will be described.

Figure 1:
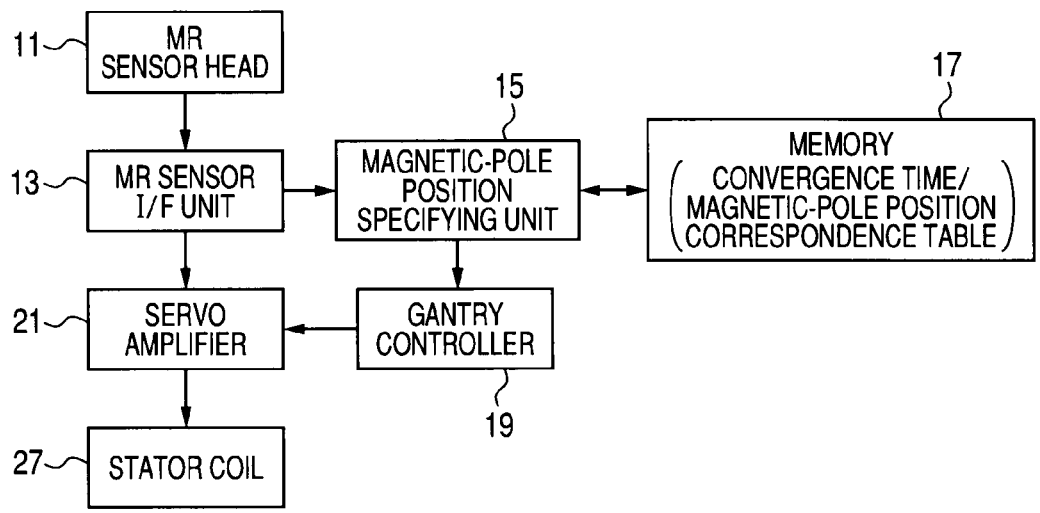
FIG. 1 is a diagram showing a configuration of a main part of an X-ray computed tomographic apparatus according to an embodiment.
Figure 2A:
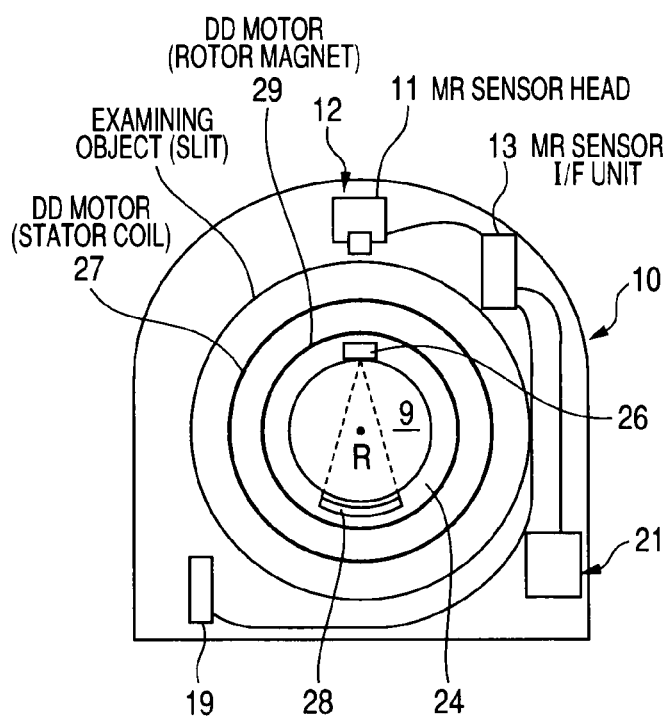
FIGS. 2A and 2B are diagrams showing an internal structure of a gantry shown in FIG. 1.
Figure 2B:
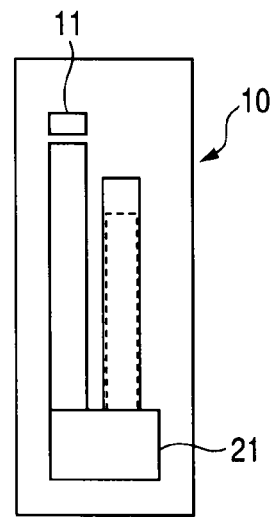

As shown in FIGS. 1, 2A, and 2B, the X-ray computed tomographic apparatus according to the embodiment includes a gantry 10. The gantry 10 includes an opening 9. At a data-collection time, the subject on a bed is disposed in the opening 9. The gantry 10 includes a substantially annular rotary frame 24. The rotary frame 24 is mounted with an X-ray tube 26 and an X-ray detector 28. The X-ray detector 28 is opposed to the X-ray tube 26 with the subject interposed therebetween. The X-ray detector 28 detects the X-ray transmitted to the subject. Although it is not shown in the drawings, a high voltage generator generates a current in a filament supplied to the X-ray tube 26 and generates a tube voltage applied to the X-ray tube 26.

A data collector (not shown) collects a data showing a transmitted X-ray amount detected by the X-ray detector 28 and supplies the data to a tomographic-image reconstruction process. The reconstructed tomographic image is displayed on a monitor.

Figure 3:
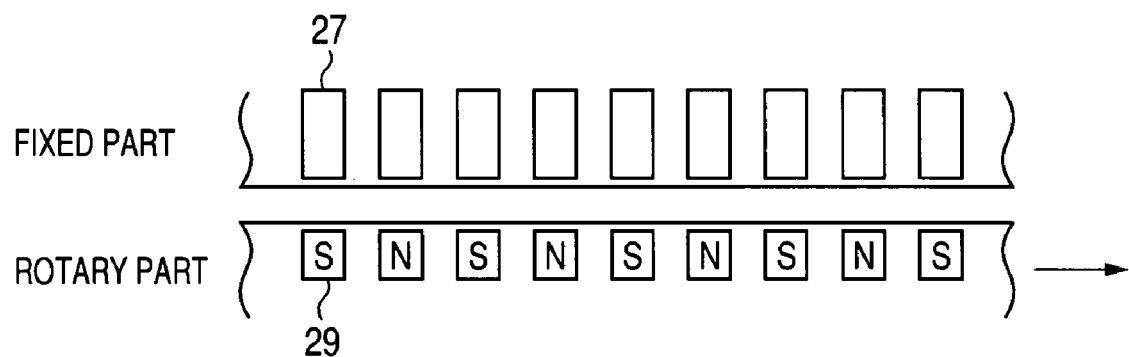
FIG. 3 is a diagram showing a part of an arrangement of a stator coil and a rotor magnet shown in FIG. 2.

In order to drive the rotation of the rotary frame 24 supported to the gantry so as to be rotatable about a rotary center axis R, a direct-drive motor is used. As shown in FIG. 3, the direct-drive motor includes a plurality of rotor magnets 29 arranged in the outer periphery of the rotary frame 24 in an annular shape and a plurality of stator coils 27 arranged in a fixed part in an annular shape so as to be opposed to the rotor magnets 29.

An MR sensor head 11 of an MR (magnetic-resistance) sensor 12 for detecting a magnetic-flux variation is provided in the vicinity of the stator coils 27 arranged in the fixed part. When the rotary frame 24 and the rotor magnets 29 rotate together, the MR sensor head 11 detects the magnetic-flux variation caused by the rotation. An MR sensor I/F unit 13 continuously and repeatedly outputs encoding pulses during the time when the MR sensor head 11 detects the magnetic-flux variation, that is, during the rotation of the rotor magnets 29.

A servo amplifier 21 supplies a driving current to the stator coils 27 in accordance with a control signal transmitted from a gantry controller 19. Additionally, the gantry controller 19 controls a driving-current amplitude and a magnetism changing timing.

A magnetic-pole position specifying unit 15 specifies the magnetic-pole position of the rotor magnet 29 during a magnetic-pole position specifying operation on the basis of the encoding pulses output from the MR sensor I/F unit 13 of the MR sensor 12. Additionally, at an actual scanning operation, the magnetism changing timing is determined by the control signal transmitted from the gantry controller 19 with respect to the magnetic-pole position of the rotor magnets 29.

Figure 4:
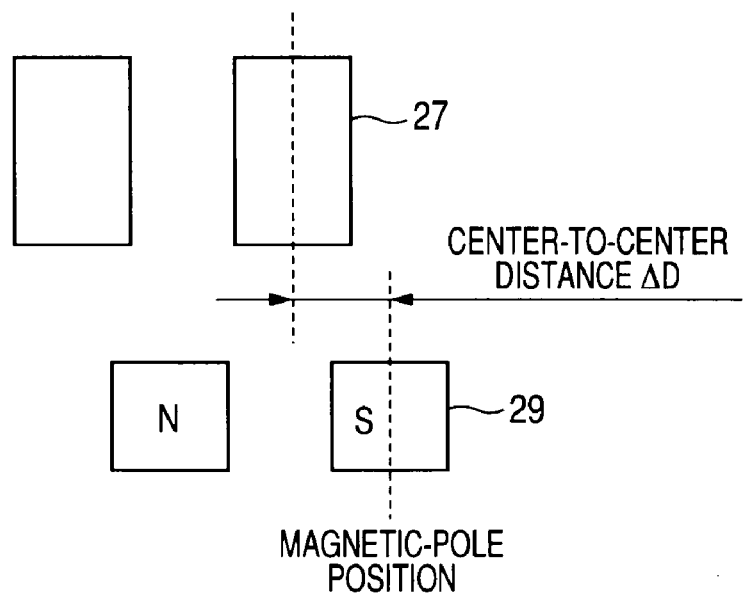
FIG. 4 is a diagram showing a definition of a rotor magnet position with respect to the stator coil (magnetic-pole position) shown in FIG. 2.

As shown in FIG. 4, the magnetic-pole position is defined as, for example, a center-to-center distance ΔD between the center of each stator coil 27 and the center of each rotor magnet 29. The magnetic-pole position is determined on the basis of an original characteristic such as a center of gravity or a strain of the rotary frame 24. The magnetic-pole position is normally maintained at the approximately same position while stopping the excitation of the stator coil 27. In accordance with the distance ΔD, a delay time until the first reversal of polarity after the driving current starts to be supplied from the servo amplifier 21 to the stator coil 27 is adjusted.

As described above, the magnetic-pole position corresponds to the center-to-center distance ΔD between the center of the stator coil 27 and the center of the rotor magnet 29. In accordance with the distance ΔD, a time until a vibration stops after a current is supplied to the stator coil 27 in a short time to vibrate the rotary frame 24, that is, a duration from a time point when a supply of a excitation current stops to a time point when a vibration of the rotor magnet 29 stops (referred to as a convergence time) is almost determined. In this embodiment, the magnetic-pole position is presumed on the basis of the convergence time. For this reason, a memory 17 stores a data of a correspondence table between a plurality of convergence time and a plurality of magnetic-pole positions. Additionally, the memory 17 stores a data of a plurality of correspondence tables between the convergence time and the magnetic-pole position having different excitation current values.

Figure 5:
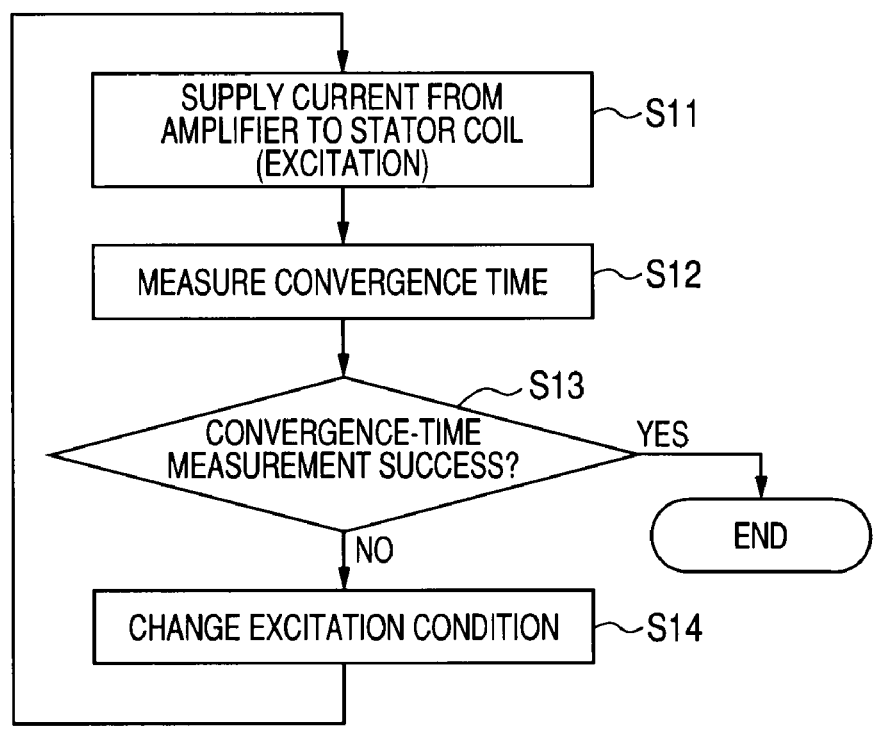
FIG. 5 is a flowchart showing a magnetic-pole position specifying procedure according to the embodiment.
Figure 6:
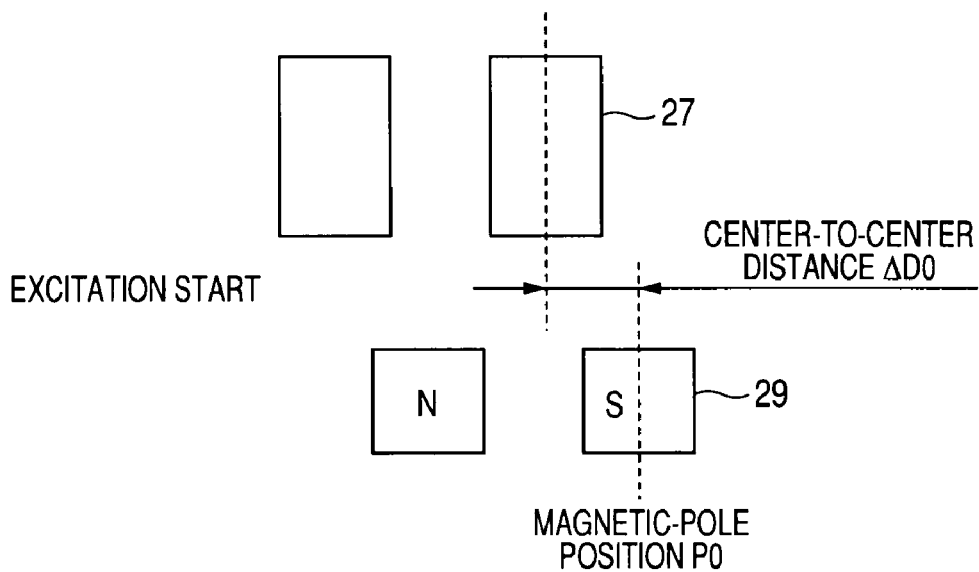
FIG. 6 is a diagram showing a state at an excitation start time according to the embodiment.
Figure 7:
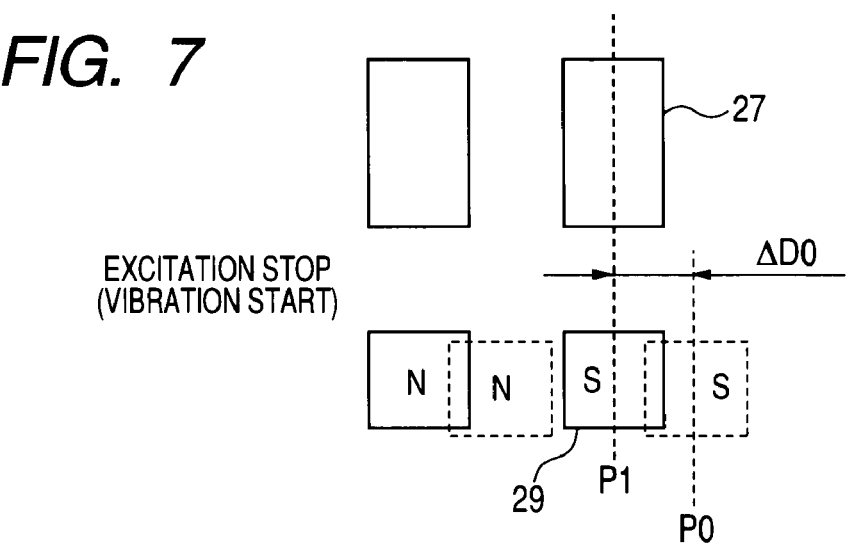
FIG. 7 is a diagram showing a state at an excitation stop time according to the embodiment.
Figure 8:
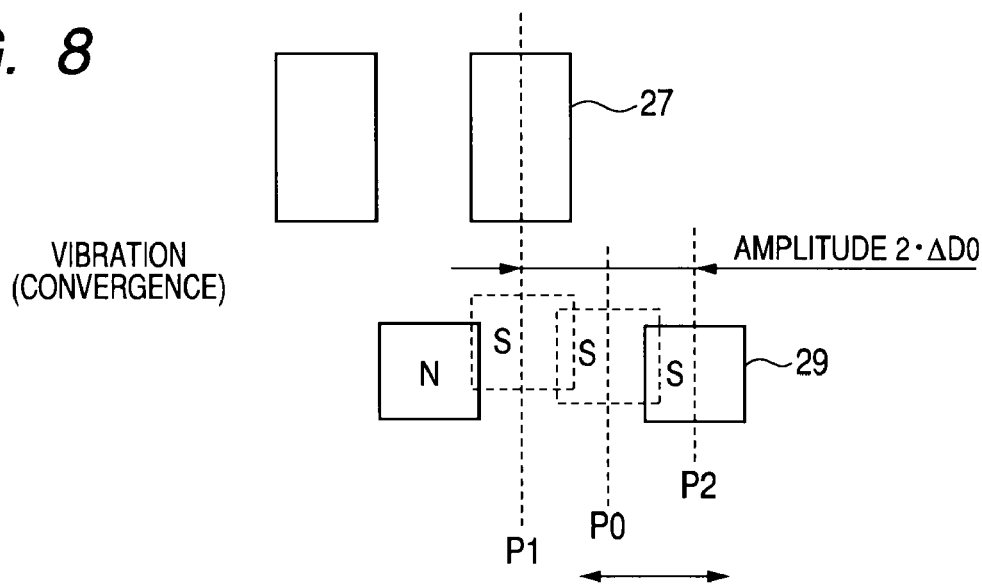
FIG. 8 is a diagram showing a vibration state according to the embodiment.
Figure 9:
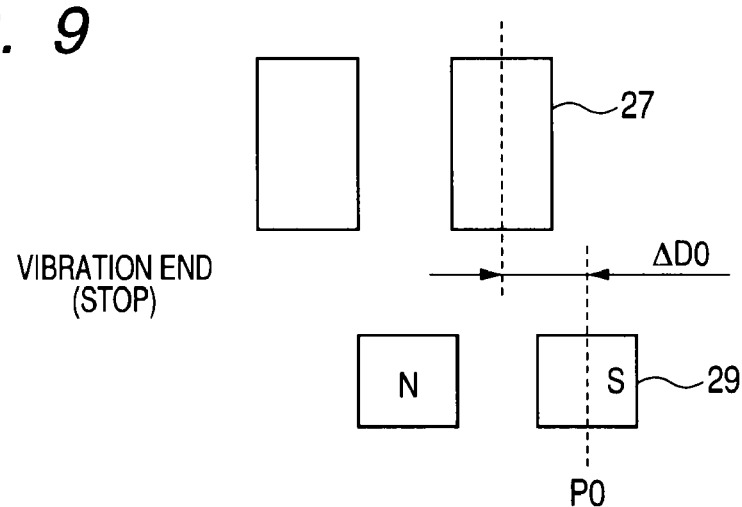
FIG. 9 is a diagram showing a sate at a vibration end time according to the embodiment.

FIG. 5 shows a procedure of the magnetic-pole position specifying operation according to the embodiment. The magnetic-pole position specifying operation starts in such a manner that a user performs a predetermined operation to the gantry controller 19 to start a magnetic-pole position specifying operation function. As shown in FIG. 6, in the initial state of the magnetic-pole position specifying operation, the magnetic-pole position is P0 and the center-to-center distance between the center of the stator coil 27 and the center of the rotor magnet 29 is ΔD0. From this initial state of the magnetic-pole position specifying operation, the gantry controller 19 supplies a control signal to the servo amplifier 21 so as to supply a current having a predetermined polarity and a predetermined amplitude to the stator coil 27 in a predetermined extremely-short time, and the servo amplifier 21 supplies a current having a predetermined polarity and a predetermined amplitude to the stator coil 27 in a predetermined extremely-short time (S11). Accordingly, the stator coil 27 is excited, and as shown in FIG. 7, the rotor magnet 29 moves together with the rotary frame 24. When the supply of the current stops, as shown in FIG. 8, the vibration of the rotary frame 24 starts from the current position.

The magnetic-pole position specifying unit 15 measures the number of encoding pulses until the encoding pulse stops from a time point when the supply of the current stops, that is, the vibration starts, that is, until a convergence time that the convergence of the vibration is carried out to thereby stop the rotary frame 24 (S12). The magnetic-pole position specifying unit 15 specifies the magnetic-pole position on the basis of the magnetic-pole position (distance ΔD0) corresponding to the number of the encoding pulses until the convergence time or a value corresponding to the convergence time read out from the memory 17, and ends the operation.

Here, a rotary torque of the rotary frame 24 reduces in accordance with a load variation caused by an abrasion of a brush of a slip ring, an insufficient adjustment of a rotary balance, and a variation in time of a bearing. For this reason, the operation may stop without successfully measuring the convergence time in some cases. For example, when the magnetic-pole position specifying unit 15 determines that the urged rotary frame 24 keeps rotating in one direction without a vibration and the measured convergence time exceeds a predetermined upper-limit time (S13), the gantry controller 19 changes the excitation condition and for example, decreases the current value of the excitation current supplied from the servo amplifier 21 to the stator coil 27 by a predetermined amplitude (S14). Alternatively, the current supply time may reduce by a predetermined time instead of decreasing the current amplitude.

As the condition, the excitation current is supplied from the servo amplifier 21 to the stator 27 (S11), and the convergence time is measured by the magnetic-pole position specifying unit 15 (S12). Then, the magnetic-pole position specifying unit 15 determines whether the convergence time exceeds the predetermined upper-limit time (S13). When the convergence time is not more than the predetermined upper-limit time, a correspondence table corresponding to the current value of the excitation current is selectively used to specify the magnetic-pole position corresponding to the convergence time, and ends the operation.

In S13, when the convergence time exceeds again the predetermined upper-limit time, the gantry controller 19 changes again the excitation condition (S14). Accordingly, the amplitude of the current supplied from the servo amplifier 21 to the stator coil 27 further decreases by a predetermined amplitude (S11), and the convergence time is measured again.

Likewise, the convergence-time measurement is repeated by decreasing the excitation condition until the convergence time is not more than the predetermined upper-limit time.

In this way, the excitation condition for each step from the optimal condition to the worst state is changed in consideration of the load variation caused by the abrasion of the brush, the insufficient adjustment of the rotary balance, and the variation in time of the bearing. When the load reduces to thereby reduce a friction torque, the convergence time until the magnetic pole is detected becomes longer due to this function. In terms of the magnetic-pole specifying method, it is possible to successfully measure the magnetic-pole position all the time even in any load variation condition. Accordingly, it is possible to realize an improvement in reliability of the apparatus, a reduction in the number of components, a reduction in a frequency of breakdown, and a reduction in cost. It is advantageous to appeal the performance of the apparatus when the apparatus is continuously used in the optimal condition.

Additionally, a status in which the excitation condition gradually decreases is transmitted to the gantry controller 19 and a host controller of the CT apparatus. The fact that the excitation condition is gradually decreased may be stored as a log file by the host controller or may be used as a trigger for checking a state of the gantry (the abrasion state of the brush, the state of the bearing, and the insufficient adjustment of the rotary balance). By checking such states, a service engineer is capable of using such states as information for determining the optimal timing of the brush exchange, the necessity of the balance check, and the necessity of the bearing exchange.

The invention is not limited to the above-described embodiments, but may be modified in various forms without departing from the spirit and scope of the invention. Various inventions may be appropriately formed in a combination with a plurality of constituents shown in the above-described embodiments. For example, some constituents may be omitted from all constituents shown in the above-described embodiments. Then, the constituents shown in different embodiments may be appropriately used in a combination.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
   a rotary frame;
   a mechanism which rotatably supports the rotary frame;
   an X-ray tube which is mounted to the rotary frame;
   an X-ray detector which is mounted to the rotary frame;
   a plurality of rotor magnets which is arranged in the rotary frame;
   a plurality of stator coils which is opposed to the rotor magnets;
   a sensor which detects a magnetic-flux variation accompanied by a movement of the rotor magnets; and
   a position specifying unit which specifies a magnetic-pole position of each rotor magnet with respect to each stator coil on the basis of an output of the sensor and a convergence time from a vibration start of the rotary frame caused by a short-time excitation of the stator coil to a vibration stop of the rotary frame.

2. The X-ray computed tomographic apparatus according to claim 1, further comprising:
   a storage unit which stores a correspondence table between the convergence time and the magnetic-pole position.

3. The X-ray computed tomographic apparatus according to claim 1, further comprising:
   a storage unit which stores a plurality of correspondence tables between the convergence time and the magnetic-pole position having different excitation current values.

4. The X-ray computed tomographic apparatus according to claim 3, wherein the position specifying unit selectively uses the plurality of correspondence tables in accordance with the excitation current values.

5. The X-ray computed tomographic apparatus according to claim 1, wherein the position specifying unit determines whether the convergence time exceeds a predetermined time.

6. The X-ray computed tomographic apparatus according to claim 5, further comprising:
   a controller which decreases the excitation current value of the stator coil when it is determined that the convergence time exceeds the predetermined time.

7. An X-ray computed tomographic apparatus comprising:
   a rotary mechanism which rotates an X-ray tube and an X-ray detector;
   a direct-drive motor which is mounted to the rotary mechanism; and
   a position specifying unit which specifies a magnetic-pole position of a rotor magnet with respect to a stator coil on the basis of a convergence time from a vibration start of a frame caused by a short-time excitation of the stator coil to a vibration stop of the frame.

8. The X-ray computed tomographic apparatus according to claim 7, further comprising:

a storage unit which stores a correspondence table between the convergence time and the magnetic-pole position.

9. The X-ray computed tomographic apparatus according to claim 7, further comprising:
a storage unit which stores a plurality of correspondence tables between the convergence time and the magnetic-pole position having different excitation current values.

10. The X-ray computed tomographic apparatus according to claim 9, wherein the position specifying unit selectively uses the plurality of correspondence tables in accordance with the excitation current values.

11. The X-ray computed tomographic apparatus according to claim 7, wherein the position specifying unit determines whether the convergence time exceeds a predetermined time.

12. The X-ray computed tomographic apparatus according to claim 11, further comprising:
a controller which decreases the excitation current value of the stator coil when it is determined that the convergence time exceeds the predetermined time.

13. An apparatus comprising:
a rotary mechanism;
a direct-drive motor which is mounted to the rotary mechanism; and
a position specifying unit which specifies a magnetic-pole position of a rotor magnet with respect to a stator coil or a value corresponding to the magnetic-pole position on the basis of a convergence time from a vibration start of a frame caused by a short-time excitation of the stator coil to a vibration stop of the frame or a value corresponding to the convergence time.

* * * * *